(12) United States Patent
Mannheimer et al.

(10) Patent No.: US 8,855,734 B2
(45) Date of Patent: *Oct. 7, 2014

(54) MEDICAL SENSOR AND TECHNIQUE FOR USING THE SAME

(71) Applicant: Covidien LP, Mansfield, MA (US)

(72) Inventors: Paul D. Mannheimer, Danville, CA (US); Bruce R. Bowman, Eden Prairie, MN (US); Lee M. Middleman, Portola Valley, CA (US); Clark R. Baker, Jr., Newman, CA (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/717,380

(22) Filed: Dec. 17, 2012

(65) Prior Publication Data

US 2013/0109936 A1 May 2, 2013

Related U.S. Application Data

(62) Division of application No. 12/005,023, filed on Dec. 21, 2007, now Pat. No. 8,352,004.

(51) Int. Cl.
| | | |
|---|---|---|
| *A61B 5/1455* | (2006.01) | |
| *A61B 5/145* | (2006.01) | |
| *A61B 5/00* | (2006.01) | |
| *A61B 5/01* | (2006.01) | |
| *A61B 5/0205* | (2006.01) | |
| *A61B 5/053* | (2006.01) | |

(52) U.S. Cl.
CPC .......... *A61B 5/02055* (2013.01); *A61B 5/14552* (2013.01); *A61B 5/14546* (2013.01); *A61B 5/6831* (2013.01); *A61B 5/4875* (2013.01); *A61B 5/6829* (2013.01); *A61B 5/01* (2013.01); *A61B 5/6843* (2013.01); *A61B 5/0531* (2013.01); *A61B 5/7246* (2013.01)
USPC ............ 600/310; 600/344; 600/322; 600/323

(58) Field of Classification Search
USPC .................................................. 600/310–344
See application file for complete search history.

(56) References Cited

U.S. PATENT DOCUMENTS

| | | | | |
|---|---|---|---|---|
| 5,119,463 A | * | 6/1992 | Vurek et al. .................... | 385/129 |
| 5,601,079 A | * | 2/1997 | Wong et al. .................... | 600/322 |
| 7,006,855 B1 | * | 2/2006 | Sarussi .......................... | 600/310 |
| 7,389,131 B2 | * | 6/2008 | Kanayama .................... | 600/322 |

* cited by examiner

*Primary Examiner* — Eric Winakur
*Assistant Examiner* — Marjan Fardanesh
(74) *Attorney, Agent, or Firm* — Fletcher Yoder PC

(57) ABSTRACT

In an embodiment, a sensor may be adapted to provide information related to its position on a patient's tissue. The sensor may include tissue contact sensors which may relay a signal related to the proper placement of the sensor relative to the tissue of a patient. Such a sensor may be useful for providing information to a clinician regarding the location of the sensor in relation to the skin of a patient in order to provide improved measurements.

13 Claims, 8 Drawing Sheets

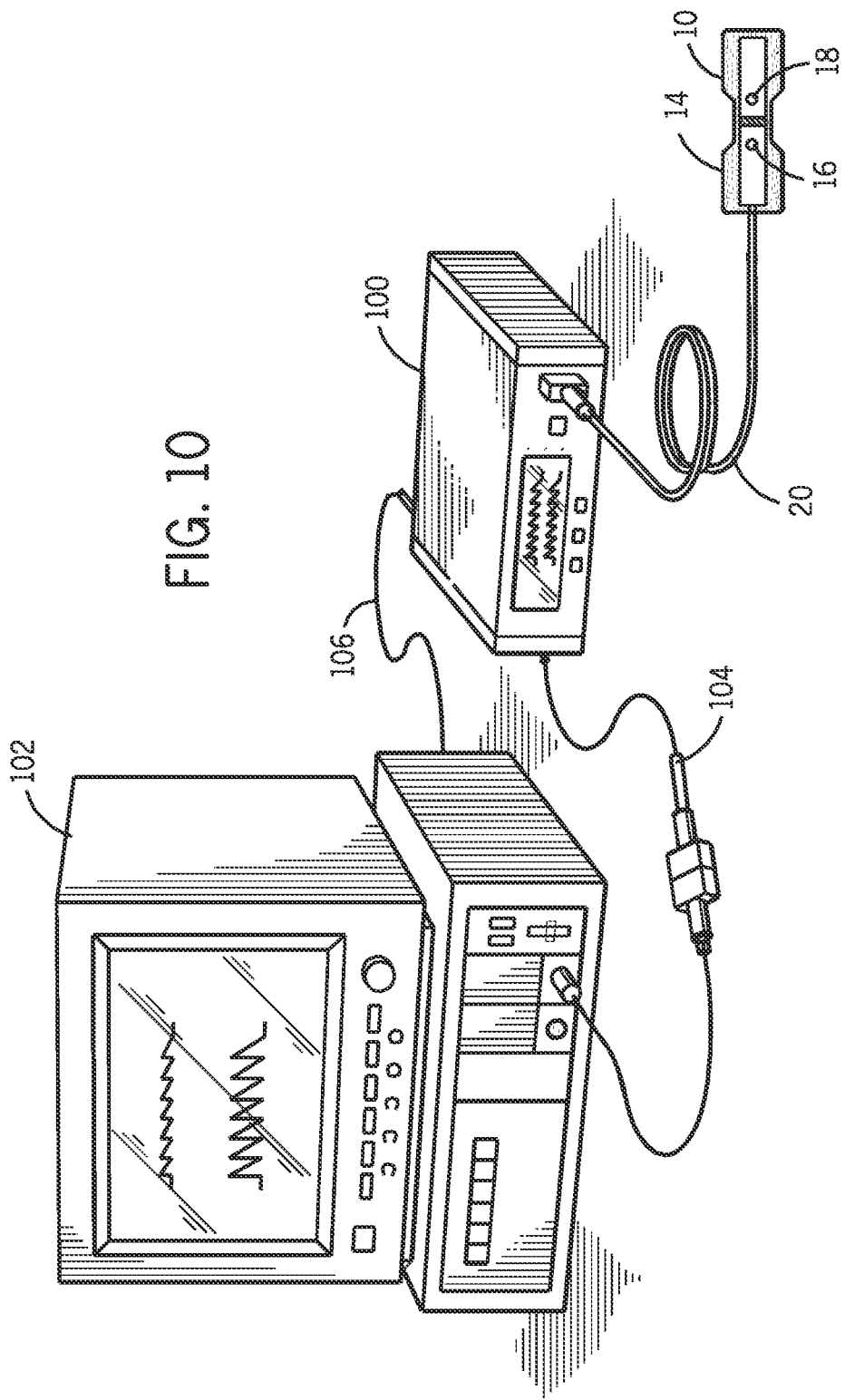

MEDICAL SENSOR AND TECHNIQUE FOR USING THE SAME

CROSS-REFERENCE TO RELATED APPLICATION

This application is a divisional of U.S. application Ser. No. 12/005,023, entitled "MEDICAL SENSOR AND TECHNIQUE FOR USING THE SAME," filed on Dec. 21, 2007, the disclosure of which is hereby incorporated by reference in its entirety for all purposes.

BACKGROUND

The present disclosure relates generally to medical devices and, more particularly, to sensors used for sensing physiological parameters of a patient.

This section is intended to introduce the reader to various aspects of art that may be related to various aspects of the present disclosure, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the field of medicine, doctors often desire to monitor certain physiological characteristics of their patients. Accordingly, a wide variety of devices may have been developed for monitoring many such physiological characteristics. Such devices may provide doctors and other healthcare personnel with information they may utilize to provide the best possible healthcare for their patients. As a result, such monitoring devices may have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the oxygen saturation of hemoglobin in arterial blood, the volume of individual blood pulsations supplying the tissue, and/or the rate of blood pulsations corresponding to each heartbeat of a patient. The "pulse" in pulse oximetry may refer to the time varying amount of arterial blood in the tissue during each cardiac cycle.

Pulse oximeters may utilize a non-invasive sensor capable of transmitting light through a patient's tissue and that photoelectrically detects the absorption and/or scattering of the transmitted light in such tissue. Physiological characteristics may then be calculated based at least in part upon the amount of light absorbed or scattered. The light passed through the tissue may be typically selected to be of one or more wavelengths that may be absorbed or scattered by the blood in an amount correlative to the amount of the blood constituent present in the blood. The amount of light absorbed and/or scattered may then be used to estimate the amount of blood constituent in the tissue using various algorithms.

To facilitate accurate and reliable measurements when monitoring physiological characteristics of a patient, a pulse oximetry sensor should be adequately in contact with the patient's tissue. When a sensor is dislodged or removed from the patient, or contact is inadequate, some or all of the emitted light does not pass through the patient's tissue, and the detected light may no longer relate in the same way to a physiological constituent. Because detected light unrelated to a physiological constituent may result in measurement inaccuracies, it may be desirable to provide a mechanism for indicating that sensor is not in sufficient contact with the patient's tissue.

SUMMARY

Certain aspects commensurate in scope of the disclosure are set forth below. It should be understood that these aspects are presented merely to provide the reader with a brief summary of certain forms that embodiments might take and that these aspects are not intended to limit the scope of the invention and/or disclosure. Indeed, the disclosure may encompass a variety of aspects that may not be set forth below.

In an embodiment, there may be provided a sensor that includes, a sensor body, an emitter and a detector disposed on the sensor body, and a tissue contact sensor disposed adjacent the sensor body. The tissue contact sensor may be capable of providing an electrical signal related to a movement of a mechanical component of the tissue contact sensor.

In an embodiment, there may also be provided a pulse oximetry system that includes a pulse oximetry monitor and a pulse oximetry sensor capable of being operatively coupled to the monitor. In an embodiment the sensor may include, a sensor body, an emitter and a detector disposed generally adjacent the sensor body, and a tissue contact sensor disposed generally adjacent the sensor body, where the tissue contact sensor may be capable of providing an electrical signal to the monitor related to a movement of a mechanical component of the tissue contact sensor.

In an embodiment, there may be provided a method which includes, moving a mechanical component of a tissue contact sensor, disposed on a medical sensor, relative to an emitter and a detector disposed generally adjacent the medical sensor, and providing an electrical signal related to the movement of the mechanical component of the tissue contact sensor.

In an embodiment, there may be provided a method of manufacturing a sensor which includes, providing a sensor body upon which an emitter and a detector are capable of being disposed, and providing a tissue contact sensor disposed generally adjacent the sensor body, wherein the tissue contact sensor may be capable of providing an electrical signal related to a movement of a mechanical component of the tissue contact sensor.

BRIEF DESCRIPTION OF THE DRAWINGS

Aspects of embodiments may become apparent upon reading the following detailed description and upon reference to the drawings in which:

FIG. 10 illustrates a pulse oximetry system coupled to a multi-parameter patient monitor and a sensor, according to an embodiment.

DETAILED DESCRIPTION

One or more embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

In an embodiment, medical sensors for pulse oximetry or other applications utilizing spectrophotometry may be provided which may provide a signal related to a "sensor on" and/or a "sensor off" state. In an embodiment, the sensors may include one or more tissue contact sensors. Such sensors may provide a signal to a downstream medical device in order to convey a change in sensor status medical device and to a healthcare practitioner, for example when a sensor falls off of a patient or moves relative to a patient's tissue. Further, embodiments of such sensors may be capable of providing information as to proper sensor application. By providing information related to the correct placement of a sensor, sensors as provided herein may reduce measurement errors which may result from a sensor being located too far from the tissue to provide accurate measurements, as well as other inadequate sensor placement.

Figure 1:
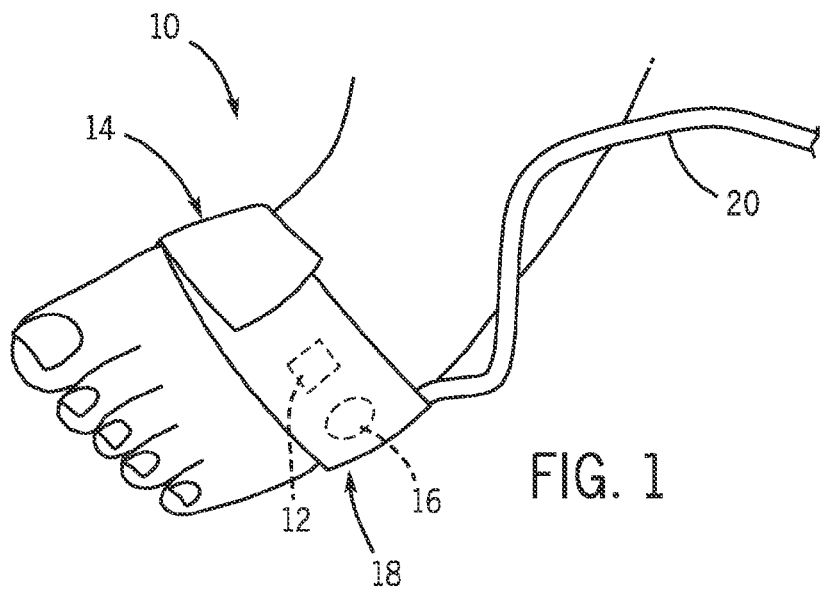
FIG. 1 illustrates a perspective view of bandage-style medical sensor including a contact sensor, according to an embodiment.

FIG. 1 shows an embodiment of a sensor 10 with a generic contact sensor 12 disposed generally adjacent and/or on a sensor body 14. As depicted in this embodiment, the sensor 10 may have a bandage-style sensor body 14, capable of conforming to a patient's foot. In an embodiment, the sensor 10 includes an emitter 16 and a detector 18. The signal from the detector 18 and the signal from the contact sensor 12 may be sent via sensor cable 20 to a downstream medical device discussed in more detail below. It should also be understood that the contact sensor 12 may be a separate assembly disposed generally adjacent and/or on the sensor body 14, or may be integral with the sensor circuit connected to the emitter 16 and the detector 18. In an embodiment, a mechanical switch contact sensor, such has those provided herein, may be electrically in series with the emitter 16. A closing or opening of a circuit may control power to the emitter 16 or the detector 18.

In an embodiment, the contact sensor 12 may be used with any suitable sensor type, including reusable and/or disposable sensors, as well as clip-on or bandage-style sensors, among others. Further, it should be understood that the contact sensor 12 may be used with sensors applied to any suitable tissue site (e.g., finger, ear, toe, and forehead). The contact sensor 12 may be disposed on the sensor body 14 in any suitable location. As depicted in this embodiment, the contact sensor 12 may be proximate to the emitter 16. In transmission-type sensors 10 in which the emitter 16 and the detector 18 are positioned across the tissue from one another, it may be advantageous to position the contact sensor 12 away from the area between the emitter 16 and the detector 18. In this case, the contact sensor 12 may not be located in an area of the sensor body 14 that may fold around the tissue and thus may not conform closely enough to provide an accurate contact signal. In an embodiment, in reflectance-type sensors in which the emitter 16 and the detector 18 are side-by-side, the contact sensor 12 may be located in any suitable location on the sensor body 14.

Figure 2A:
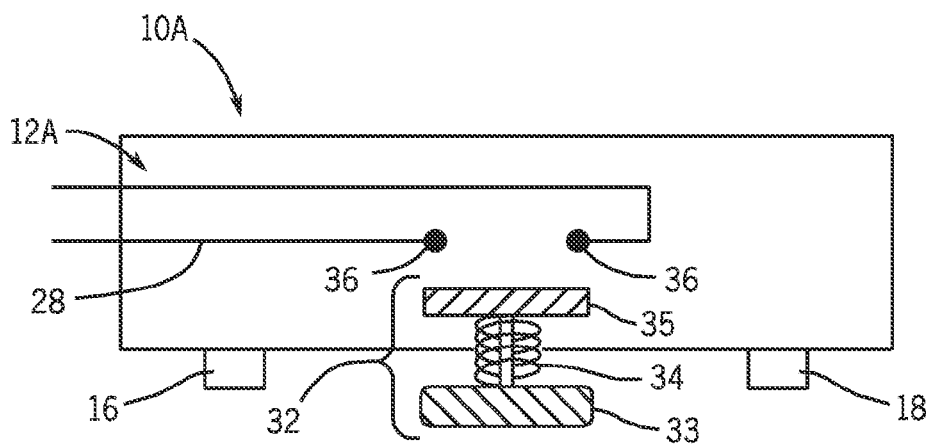
FIG. 2A is cross-sectional view of a medical sensor including a plunger-activated mechanical contact sensor, according to an embodiment.
Figure 2B:
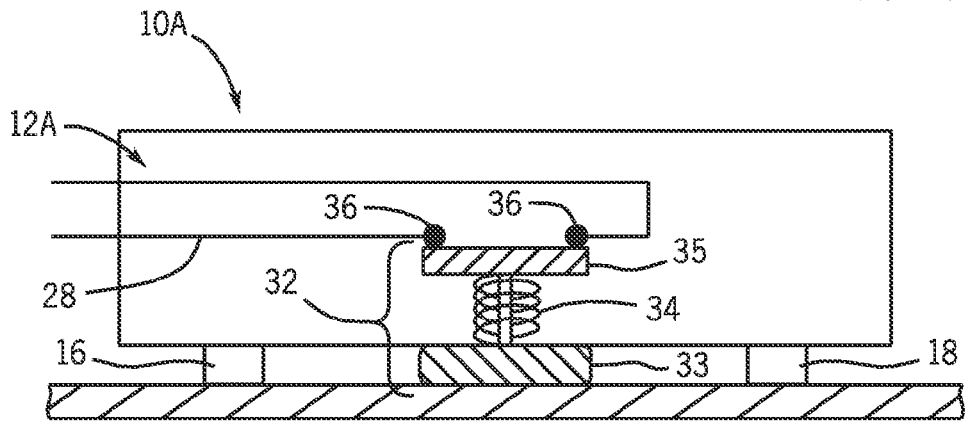
FIG. 2B is cross-sectional view of the sensor of FIG. 2A applied to a patient's tissue with the mechanical contact sensor engaged to close a circuit, according to an embodiment.

FIG. 2A and FIG. 2B illustrate an embodiment of a medical sensor 10A with a micro-switch contact sensor 12A. The micro-switch contact sensor 12A may be disposed on or generally adjacent to the sensor 10A in any appropriate location, such as between the emitter 16 and the detector 18, as depicted. The micro-switch contact sensor 12A may include a plunger assembly 32 which may be capable of closing a circuit 28 upon proper application of the sensor 10A to the probed tissue site.

In an embodiment, the plunger assembly 32 includes a tissue contact element 33, a biasing member 34, and a switch element 35. Generally, the switch element 35 may be formed from any suitable conductive material, such as a metal. The tissue contact element 33 may be formed from any suitable material that may be sufficiently resilient to transmit pressure from the tissue to the biasing member 34, while also being generally comfortable against a patient's tissue.

In an embodiment, suitable materials for forming the tissue contact element 33 may include thermoplastic polymers or metals, for example. The plunger assembly 32 may be biased by the biasing member, such as a spring 34, such that the switch element 35 will not close the circuit 28 without sufficient pressure being applied to the tissue contact element 33. This may result in the "resting state" of the circuit 28 being open. The open circuit may thus correspond to the "sensor off" state.

The spring 34 may be sized such that when the sensor 10A is properly applied against a monitoring site, the plunger assembly 32 will move, and the switch element 35 will close the circuit 28 across the contacts 36. In such an embodiment, the closed circuit may correspond to the "sensor on" state.

Figure 2C:
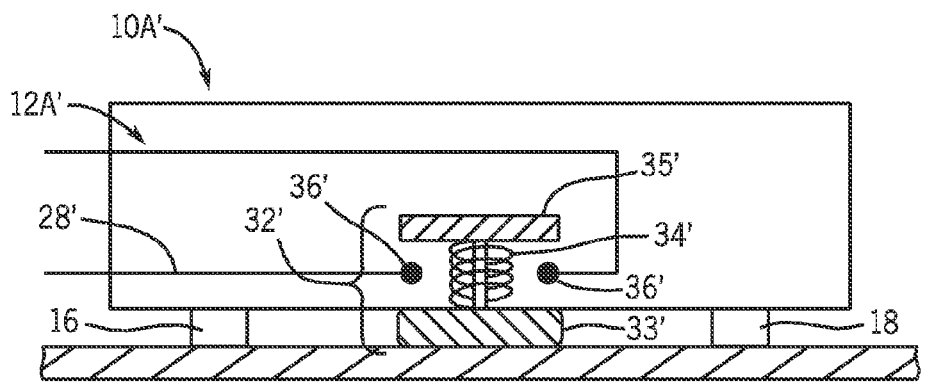
FIG. 2C shows an alternative embodiment of the sensor of FIG. 2A in which engagement of the mechanical contact sensor opens a circuit, according to an embodiment.

In an embodiment, as depicted in FIG. 2C, the plunger assembly 32' may be biased such the resting "sensor off" state of the circuit 28' is closed, and the application of force from the sensor 10A being applied to the tissue results in the switch element 35' moving to open the circuit 28'. In such an embodiment, the open circuit may correspond to the "sensor on" state.

The spring-based contact sensor 12A may provide the advantage of design flexibility as the biasing member 34 may be sized for any suitable force or pressure specification, depending on the configuration of the sensor 10A and the sensing site. Further, since the spring 34 may be configured to move only after a threshold force has been applied, the use of a spring 34 may prevent false positive "sensor on" states from incidental contact with the sensor 10A. In one embodiment, the pressure range that may be used with the spring 34 in order to close the circuit 28 may be higher than typical venous pressure (e.g., 3-5 mm Hg) and lower than typical capillary pressure (e.g., 22 mm Hg). For example, the pressure may generally be between 15 mm Hg and 20 mm Hg in an adult patient.

Figure 3A:
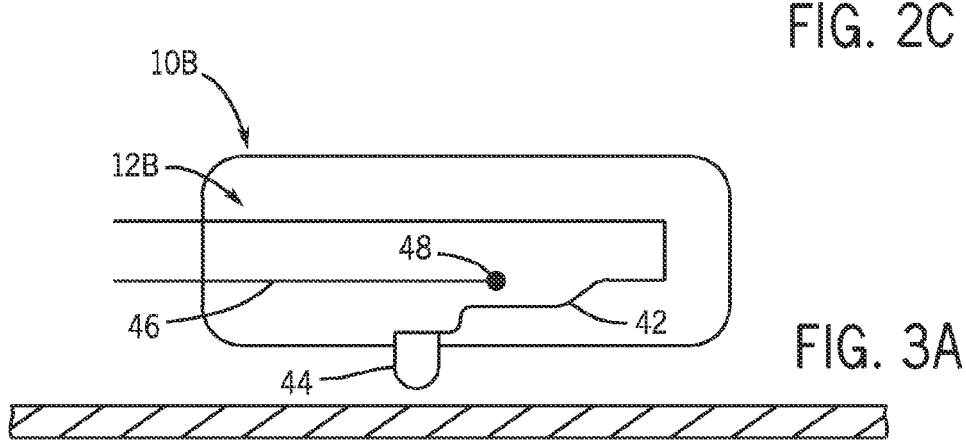
FIG. 3A is cross-sectional view of a medical sensor including an alternative mechanical contact sensor, according to an embodiment.
Figure 3B:
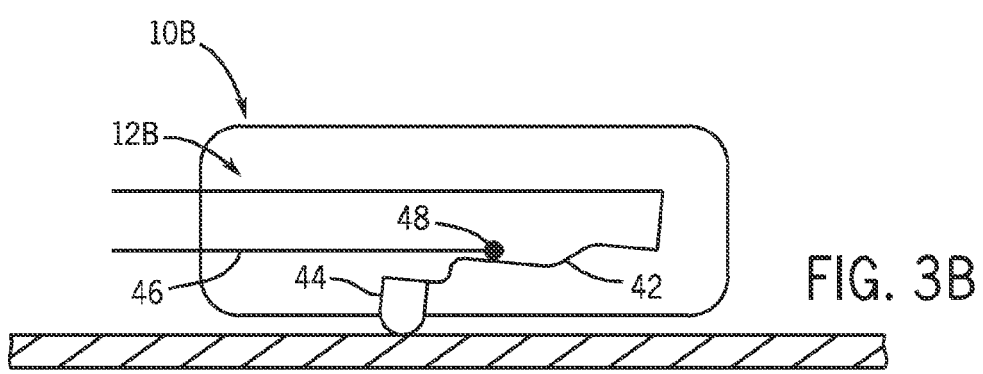
FIG. 3B is cross-sectional view of the sensor of FIG. 3A applied to a patient's tissue with the mechanical contact sensor engaged to close a circuit, according to an embodiment.
Figure 3C:
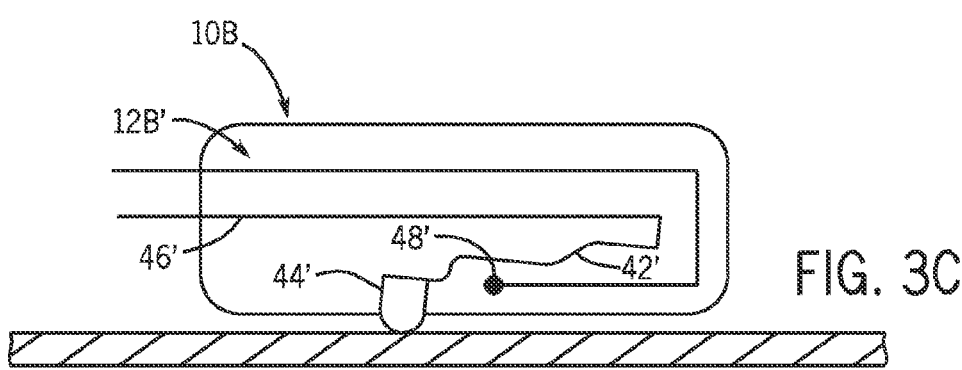
FIG. 3C shows an alternative embodiment of the sensor of FIG. 3A in which engagement of the mechanical contact sensor opens a circuit, according to an embodiment.

FIG. 3A illustrates an embodiment of a sensor 10B with a contact sensor 12B which includes a leaf spring switch 42. In an embodiment, the leaf spring switch 42 includes a tissue contact element 44 which may be capable of resting against the tissue site being probed. In an embodiment, the leaf spring switch 42 is connected to a circuit 46, such that when the sensor is in the resting "sensor off" state, the circuit 46 is open. Upon suitable pressure being applied to the leaf spring switch 42, the leaf spring switch 42 is pushed against the contact 48, causing the circuit 46 to close, resulting in a signal which may indicate that the sensor is in the "sensor on" state, as shown in FIG. 3B. Thus, the portion of the leaf spring switch 42 that closes the circuit may be formed from a suitably conductive material. In an embodiment, such a contact sensor 12B may be relatively simple in design and configuration, and lightweight. This may enable certain cost and manufacturing advantages. In an alternative embodiment, shown in FIG. 3C, the leaf spring switch 42' of the contact sensor 12B' may be biased so that the resting "sensor off" state is a closed circuit 46'. When the sensor is in close contact with the skin, the leaf spring switch 42' is pushed up, resulting in an open circuit indicating the "sensor on" state.

Figure 4:
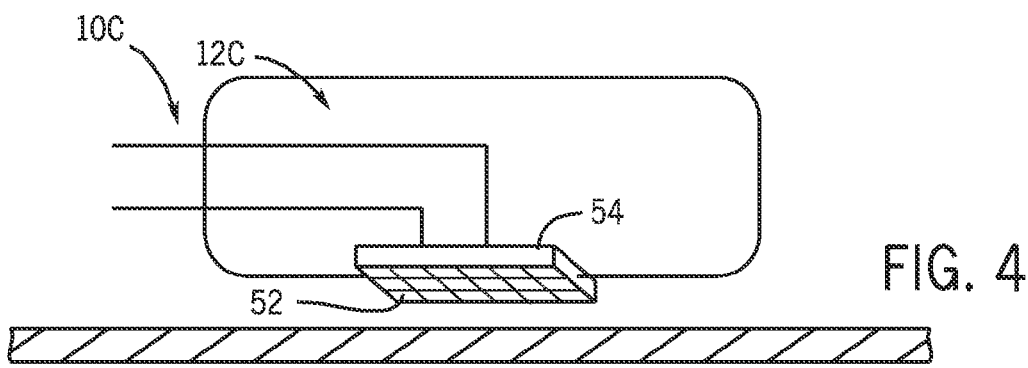
FIG. 4 illustrates an exemplary strain-gauge semiconductor contact sensor, according to an embodiment.

FIG. 4 shows an embodiment of a sensor 10C with a strain gauge contact sensor 12C. The strain gauge contact sensor 12C may incorporate a conductive grid 52 applied to a carrier matrix 54, for example a semiconductive material, that is capable of relaying a signal related to a pressure level when the sensor 10C is properly applied at a sensing site. In an embodiment, the electrical resistance of the grid may vary linearly with strain, and force or pressure on the strain gauge contact sensor 12C may be determined by measuring the change in resistance. Such a configuration may provide the advantage of relaying more detailed information about the nature of the contact rather than only an on/off signal. A downstream medical device such as a monitor, discussed below, may process the signal in order to characterize the nature of the pressure and determine if the pressure is associated with a "sensor on" or "sensor off" state, among other determinations utilizing the signal.

Figure 5A:
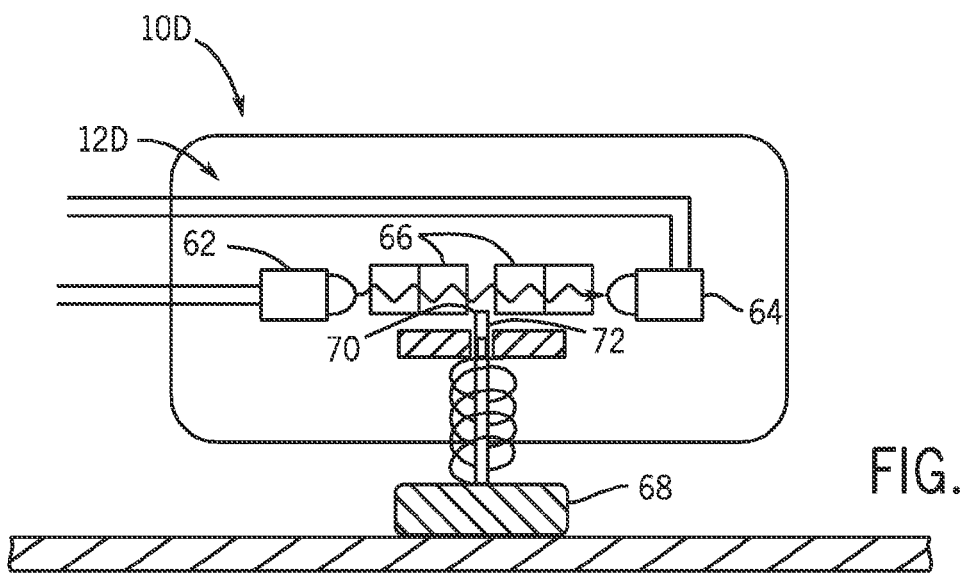
FIG. 5A illustrates an exemplary optical-type contact sensor including a mechanical plunger, according to an embodiment.
Figure 5B:
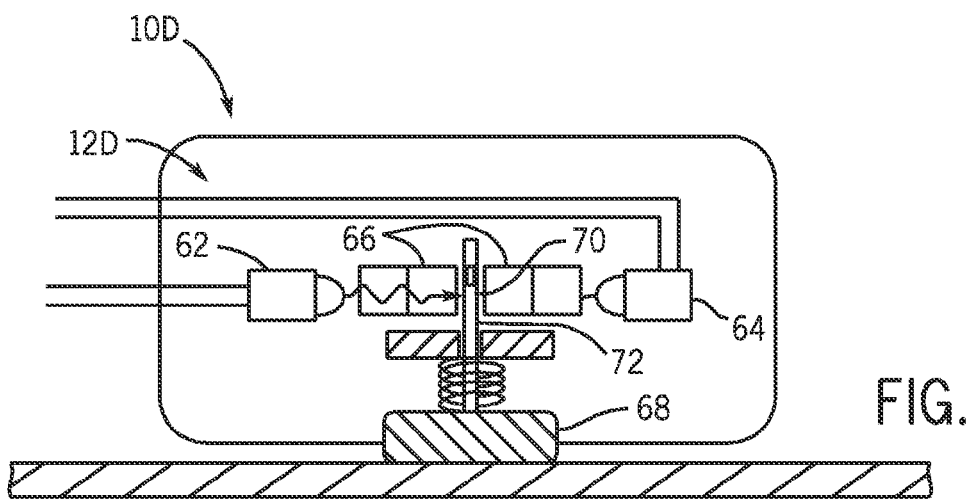
FIG. 5B is a view of the sensor of FIG. 5A applied to a patient's tissue with the optical contact blocked, according to an embodiment.

FIGS. 5A and 5B illustrate an embodiment of a sensor 10D, which may include a contact sensor 12D in which a mechanical switch may affect an optical component. In such an embodiment, a mechanical component may move within an optical path to block light from reaching a detector, or may move generally out of an optical path to allow light to reach a detector. Thus, the contact sensor 12D may relay a signal related to detected light as an indication of whether the sensor 10D is properly applied to the tissue. In addition to an emitter 16 and detector 18 (not shown) which are related to the physiological signal sensing function of the sensor 10D, the sensor 10D may also include additional optical components that are part of the contact sensor 12D.

As depicted in the embodiment in FIG. 5, the contact sensor 12D may include a secondary emitter 62 and a secondary detector 64 which are generally in-line with apertures 66 along their optical path. In an embodiment, a spring-biased plunger assembly 68 may be configured to block light or allow light to reach the secondary detector 64, depending on whether pressure is being applied to the spring biased plunger assembly 68.

The spring-biased plunger assembly 68 may move a predetermined amount upon proper application of the sensor 10D to a tissue site. The application of the sensor 10D may transmit a force to the spring-biased plunger assembly 68 which may move a shutter 70 generally out of line with the optical path between the secondary emitter 62 and the secondary detector 64, which may inhibit and/or prevent emitted light from impinging the secondary detector 64, as shown in FIG. 5B. In an embodiment, the secondary emitter 62 and the secondary detector 64 may be operatively connected to a downstream medical device, which may process the contact sensor 12D signal. Thus, the "sensor on" signal may be related to a decrease in light detected by the secondary detector 64.

In an embodiment, the shutter 70 may be positioned along the spring biased plunger assembly 68 such that the application of pressure to the contact sensor 12D may move the shutter 70 generally in-line with the optical path, and thus the "sensor on" signal may be related to an increase in detected light. In any embodiment, the shutter 70 may be positioned along a movable rod 72 which is part of the spring biased plunger assembly 68. Generally, the rod 72 may be formed from or be covered with a light absorbing material that may effectively block all or part of the light along the optical path. The shutter 70 may be a aperture or opening in the rod 72 which is suitably sized and shaped to allow some, or most of the light from the secondary emitter 62 to pass through to the detector 64.

Figure 6A:
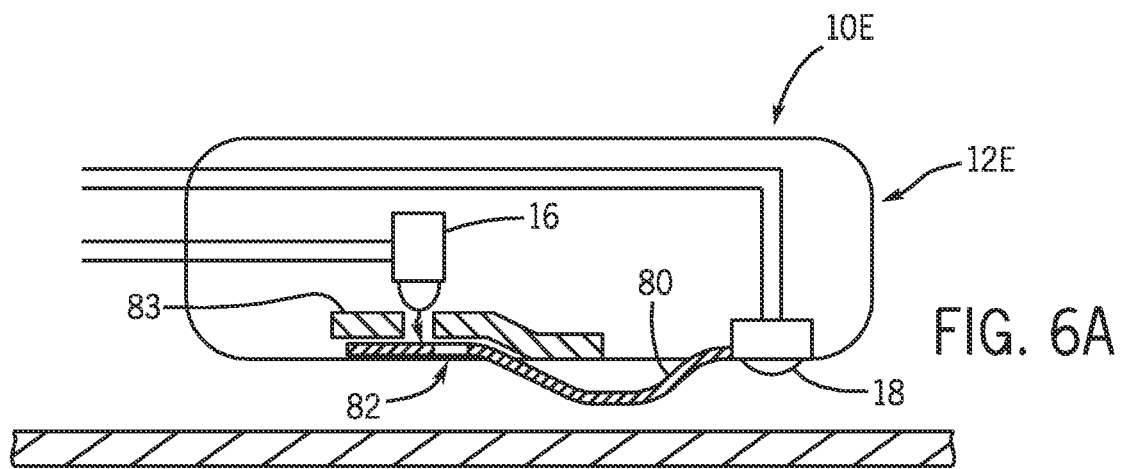
FIG. 6A illustrates an alternative optical-type contact sensor, according to an embodiment.
Figure 6B:
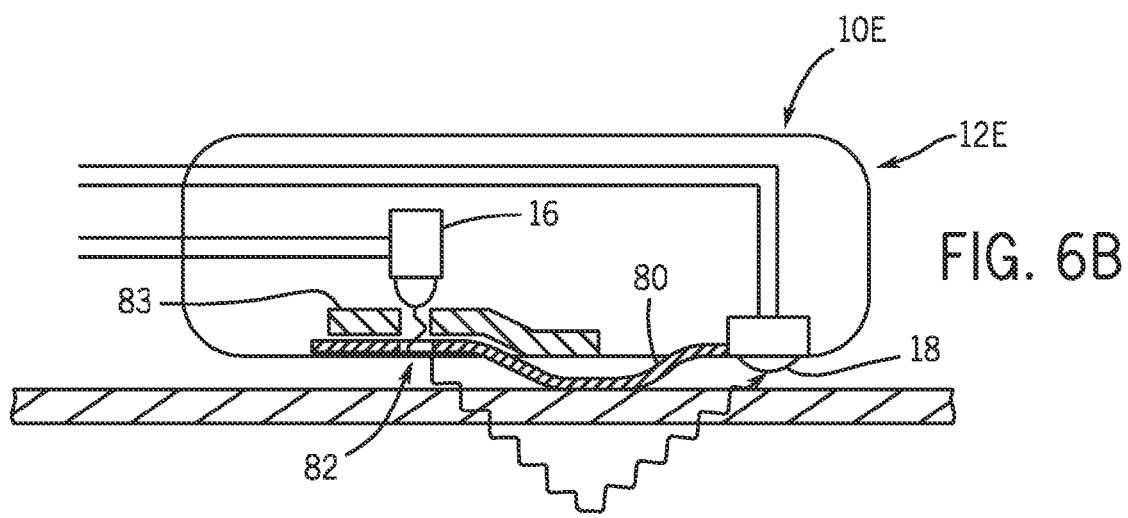
FIG. 6B is a view of the sensor of FIG. 6A applied to a patient's tissue with the optical contact opened, according to an embodiment.

FIGS. 6A and 6B illustrate an embodiment of a sensor 10E in which a contact sensor 12E includes a mechanical switch which may prevent the emitter 16 from emitting light into the tissue unless the sensor 10E has been properly applied to the patient. The pressure of application of a leaf spring 80 to the tissue site may move a shutter 82, disposed adjacent or on the leaf spring 80, into position to allow light from the emitter 16 to enter the tissue and be reflected back to the detector 18. In an embodiment, an internal light barrier 83 may provide a limited optical path for the emitted light, such that it is substantially directed towards the shutter 82. An absence of detection of emitted light may indicate to a downstream medical device as a "sensor off" condition. Such a configuration may provide the advantage of a streamlined contact sensor which is incorporated into, and provides physical feedback to, the physiological sensing components. However, such an arrangement may not allow a downstream medical device to differentiate between a nonfunctional emitter 16 and a "sensor off" condition. In such an embodiment, the downstream monitor may run a test program to check the condition emitter 16.

Figure 7A:
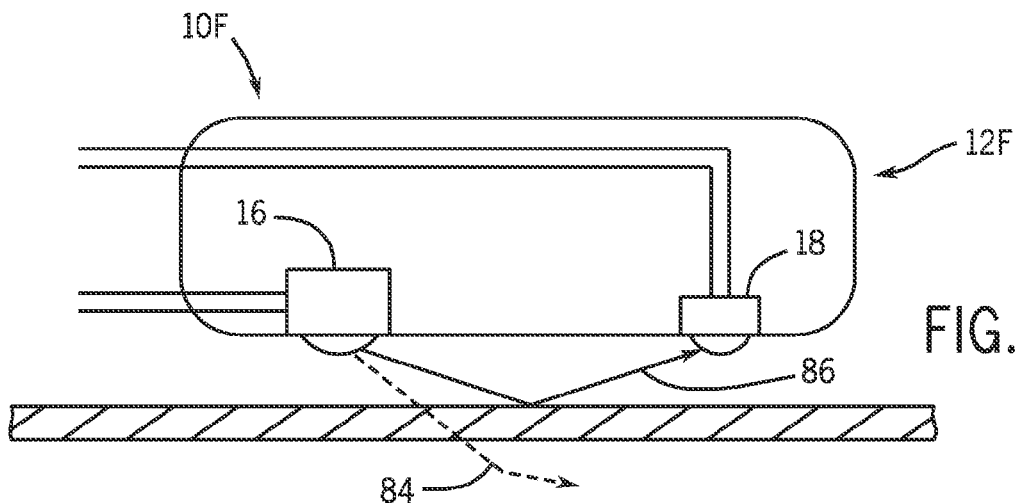
FIG. 7A illustrates an alternative optical-type contact sensor in which the sensor's emitter emits a "sensor-off" wavelength that may be detected when the sensor is not in generally adequate contact with the tissue, according to an embodiment.
Figure 7B:
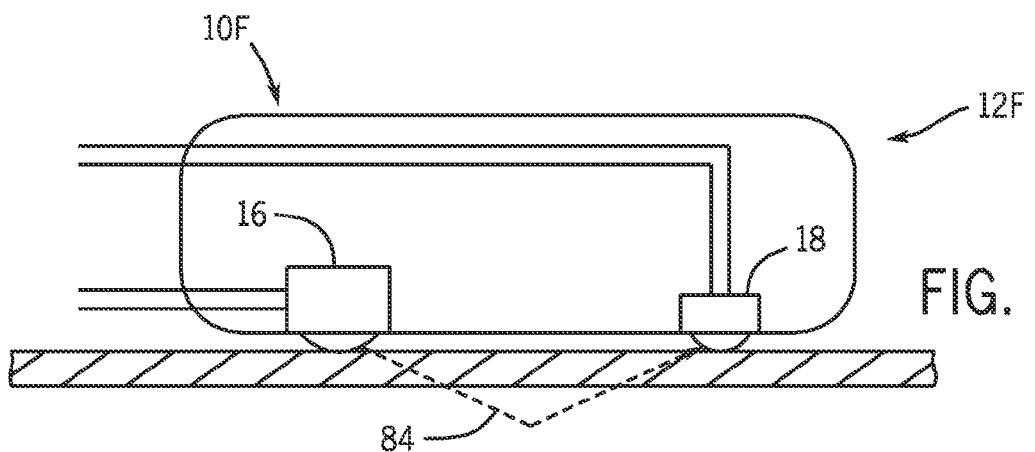
FIG. 7B is a view of the sensor of FIG. 7A applied to a patient's tissue in which the sensor's contact with the skin blocks the "sensor-off" wavelength, according to an embodiment.

In an embodiment, as shown in FIGS. 7A and 7B, a sensor 10F may include a contact sensor 12F. Contact sensor 12F may be capable of relaying an optical signal related to sensor contact utilizing particular emitted wavelengths which may be associated with a "sensor off" condition. In an embodiment, such wavelengths may be distinct from the wavelengths used to detect the physiological constituent. The wavelengths related to the "sensor off" condition may be generally strongly absorbed by the tissue, while the physiological constituent wavelengths may be generally not strongly absorbed by the tissue.

The emitter 16 may be configured to emit multiple wavelengths of light. In an embodiment, a first wavelength, as shown by dashed arrow 84, may be related to a physiological constituent. A second wavelength, as shown by solid arrow 86, may be strongly absorbed by a patient's tissue. If the sensor is not properly applied to the tissue, as shown in FIG. 7A, light of the second wavelength 86 may not be absorbed by the tissue, and may impinge the detector 18. If the sensor 10F is properly applied to the patient's tissue, light of the second wavelength 86 may be substantially absorbed by the patient's tissue, and may not impinge the detector. Furthermore, light related to the physiological constituent may properly pass through the tissue to impinge the detector 18. Thus, the "sensor off" condition may be related to an increase in light of the second wavelength 86 impinging the detector 18.

In this embodiment, such a configuration may not employ any additional mechanical components, and thus may provide manufacturing advantages. The wavelengths related to the "sensor off" condition may be selected based on the optical absorption properties of the tissue and the distance between the emitter 16 and the detector 18, among other considerations. For a pulse oximetry sensor having an emitter-detector spacing of at least a few millimeters, such a wavelength may be selected to be generally longer than about 1200 nm, so as to generally be strongly absorbed by water in the tissue, or shorter than about 600 nm, so as to be generally strongly absorbed by hemoglobin in the blood perfusing the tissue.

Figure 8:
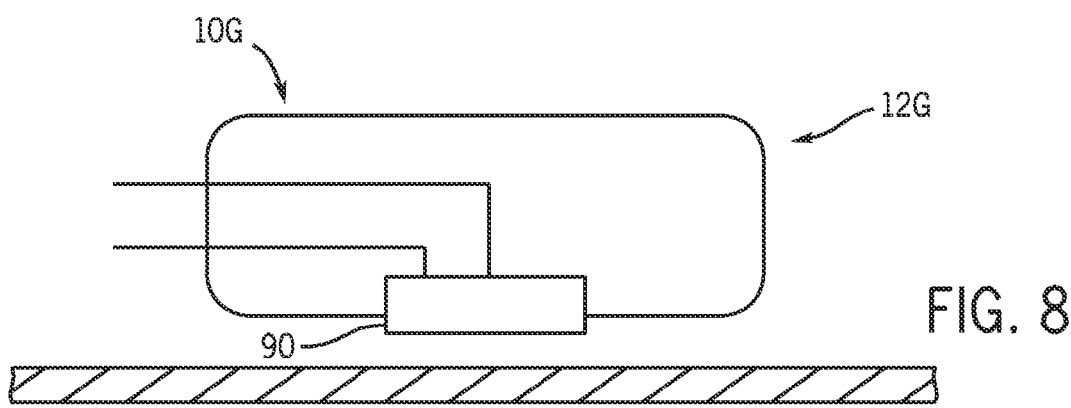
FIG. 8 illustrates an exemplary temperature contact sensor, according to an embodiment.

FIG. 8 illustrates an embodiment of a sensor 10G, in which the contact sensor 12G employs one or more temperature sensors to relay a signal related to tissue contact. The temperature sensor 90 (such as a thermistor) may be capable of measuring the temperature of the tissue site being probed. The temperature sensor 90 may provide a temperature signal which may be processed by a downstream medical device, and compared against a threshold value, such as ambient temperature, to provide an indication of a "sensor off" condition. In an embodiment, a measured temperature may be compared to a clinically determined average skin surface temperature. A significantly lower temperature measurement may indicate a "sensor off" state. In an embodiment, the contact sensor 12G of the sensor 10G may employ a plurality of temperature sensors 90 to provide additional temperature reference points. For example, when the difference between the two temperature readings is greater than a predetermined threshold value, a downstream medical device may interpret that condition as a "sensor off"

In an embodiment, a second temperature sensor (not shown) may be positioned on a non-tissue-contacting surface to measure an ambient temperature. Accordingly, when the difference between the first and second temperature measurements is less than a predetermined threshold value downstream medical device may interpret that condition as a "sensor off." The dual temperature sensing configuration, which may be more expensive than a single temperature sensing configuration, may provide a generally more reliable measurement, which may be based at least in part upon a difference between temperature measurements.

Figure 9A:
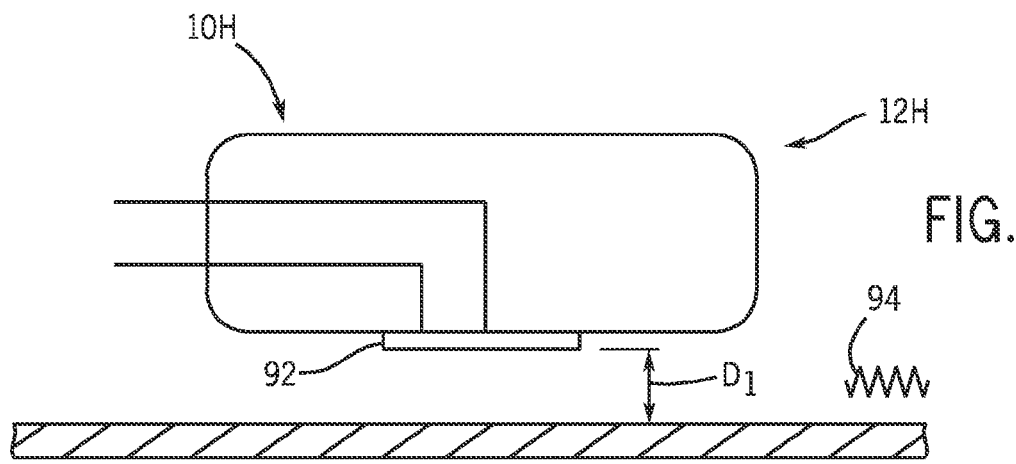
FIGS. 9A and 9B illustrate an exemplary electrode contact sensor, according to an embodiment.
Figure 9B:
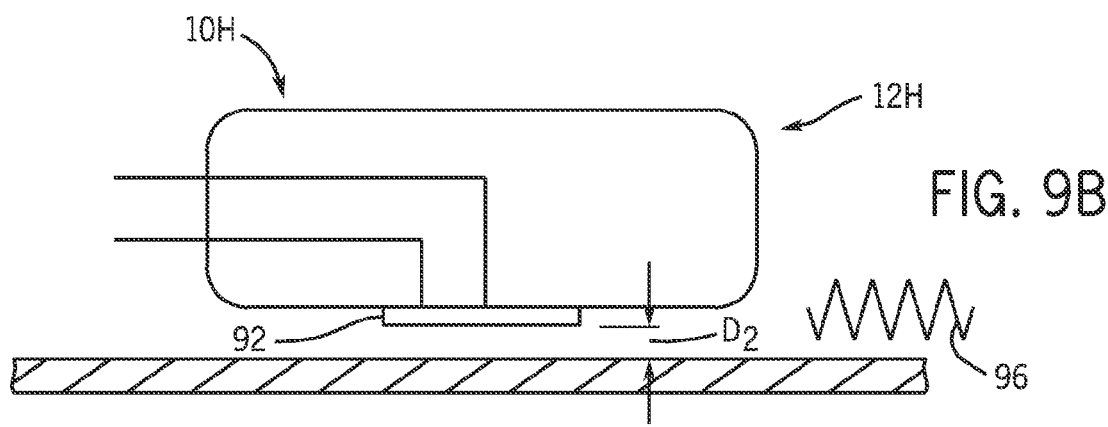

In addition to contact measurements based on mechanical switches, optical measurements, and temperature, a sensor contact with the tissue may be determined from electrical properties inherent to certain sensing components. In an embodiment, as shown in FIGS. 9A and 9B, a sensor 10H may include a contact sensor 12H having a single electrode 92 that may provide a noise signal related to the distance of the electrode 92 from the tissue. In most patient monitoring environments, electrical noise from sources such as electric lights, nearby motors, radio transmission facilities, or other nearby electrical instrumentation, is generally present. The patient's body acts, in part, as an antenna that receives these ambient noise signals. As shown in FIG. 9A, when the distance, indicated as $D_1$, from the tissue to the electrode 92 is relatively far, the electrode 92 may be in electrical-ohmic isolation from the skin and the detected noise signal, indicated by reference numeral 94, may be relatively small. As the distance between the tissue and the electrode 92 decreases, as shown in FIG. 9B, the detected noise signal, indicated by reference numeral 96, may be relatively larger. The noise signal 94 detected by the electrode 92 may be compared to a predetermined threshold corresponding with good sensor placement. For example, if the noise signal 94 is sufficiently large, the sensor 10H may be determined to be in close contact with the skin.

Such a configuration may provide cost and convenience advantages over dual electrode contact sensors that measure impedance of the skin between two electrodes. For dual electrode sensors, electrical impedance of the skin may be affected by tissue integrity and hydration as well as by the distance between the two electrodes, which may vary. As In sensor 10H a single electrode 92 relays a noise signal related to the gap between the sensor 10H and the tissue. Accordingly, the skin itself does not conduct the detected noise signal 94. Thus, the signal may not be influenced by the tissue characteristics unique to each patient. Accordingly, the sensor 10H may be more readily calibrated than dual electrode contact sensors that measure impedance of the skin between two electrodes that send a current through the skin.

In various embodiments, regardless of the type of contact sensor 12 used, a sensor, illustrated generically as a sensor 10, may be used in conjunction with a downstream medical device, which may include a pulse oximetry monitor 100, as illustrated in FIG. 10. It should be appreciated that the cable 20 of the sensor 10 may be coupled to the monitor 100 or it may be coupled to a transmission device (not shown) to facilitate wireless transmission between the sensor 10 and the monitor 100. The monitor 100 may be any suitable pulse oximeter, such as those available from Nellcor Puritan Bennett Inc. Furthermore, to upgrade conventional pulse oximetry provided by the monitor 100 to provide additional functions, the monitor 100 may be coupled to a multi-parameter patient monitor 102 via a cable or wireless connection 104 connected to a sensor input port or via a cable or wireless connection 106 connected to a digital communication port.

Figure 11:
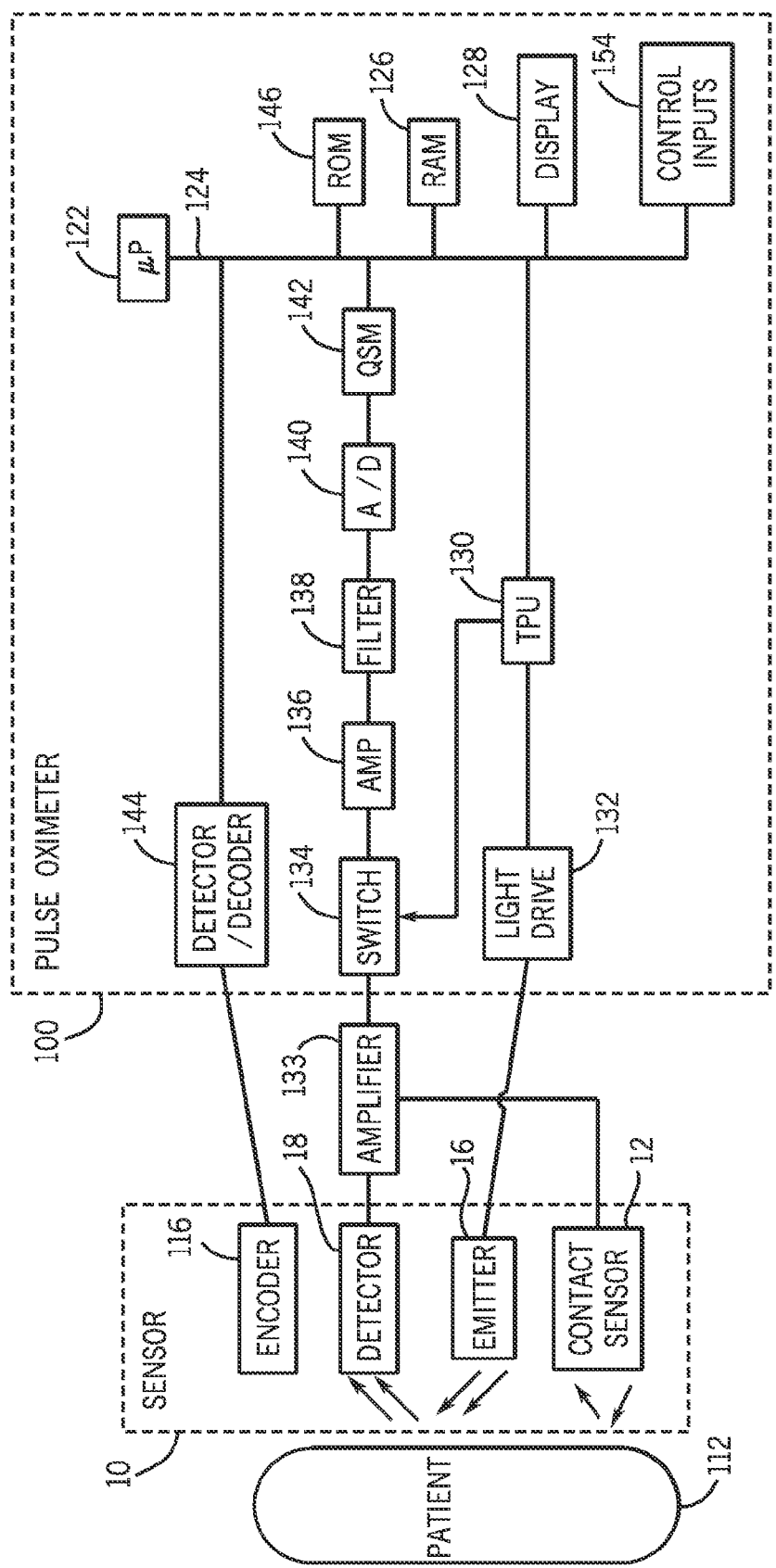
FIG. 11 is a block diagram of an exemplary pulse oximetry model connected to a sensor, according to an embodiment.

FIG. 11 is a block diagram of an embodiment of a pulse oximeter which may be configured to implement the embodiments of the present disclosure. Light from emitter 16 may pass into a blood perfused tissue 112, and may be scattered, and then detected by detector 18. A sensor 10 containing an emitter 16 and a detector 18 may also contain an encoder 116 which may be capable of providing signals indicative of the wavelength(s) of light source 16 to allow the oximeter to select appropriate calibration coefficients for calculating oxygen saturation. The encoder 116 may, in an embodiment, be a resistor. In an embodiment, the sensor 10 also includes a contact sensor 12 and may be capable of carrying a signal from the contact sensor 12 to a monitor 100.

In an embodiment, the sensor 10 may be connected to a pulse oximetry monitor 100. The monitor 100 may include a microprocessor 122 coupled to an internal bus 124. Also connected to the bus may be a RAM memory 126 and a display 128. A time processing unit (TPU) 130 may provide timing control signals to light drive circuitry 132, which controls when the emitter 16 is activated, and if multiple light sources are used, the multiplexed timing for the different light sources. TPU 130 may also control the gating-in of signals from detector 18 through an amplifier 133 and a switching circuit 134. These signals are sampled at the proper time, depending at least in part upon which of multiple light sources is activated, if multiple light sources are used. The received signal from the detector 18 and the contact sensor 12 may be passed through an amplifier 136, a low pass filter 138, and an analog-to-digital converter 140. The digital data may then be stored in a queued serial module (QSM) 142, for later downloading to RAM 126 as QSM 142 fills up. In an embodiment, there may be multiple parallel paths of separate amplifier, filter, and A/D converters for multiple light wavelengths or spectra received.

In an embodiment, the monitor 100 may be configured to receive signals from the sensor 10. The signals may be related to a physiological constituent and/or a contact sensor 12 that may be processed by the monitor 100 to indicate a sensor condition such as "sensor on" or "sensor off." The monitor 100 may be configured to provide an indication about the sensor condition, such as an audio alarm, visual alarm or a display message, such as "CHECK SENSOR." Further, the monitor 100 may be configured to receive information about the contact sensor 12 from a memory chip or other device, such as the encoder 116, which may be on the sensor 10 or the cable 20. In an embodiment, such a device may include a code or other identification parameter that may allow the monitor 100 to select an appropriate software or hardware instruction for processing the signal.

In an embodiment, a monitor 100 may run an algorithm or code for processing the signal provided by the contact sensor 12. The processing algorithm may receive information that a circuit is either opened or closed, allowing for a simple binary determination of "sensor on" or "sensor off," depending on the parameters of the particular contact sensor 12. In other embodiments, a more complex algorithm may process a signal from a primary detector 18, and/or a secondary detector, and/or other detectors, and may compare an increase or decrease in detected light to empirically-derived stored parameters to determine the sensor condition. In other embodiments, a signal may result in a hardware switch that may open or close a circuit, which may trigger the display 128 to display a sensor state message.

In an embodiment, based at least in part upon the received signals corresponding to the light received by detector 18, microprocessor 122 may calculate the oxygen saturation using various algorithms. These algorithms may require coefficients, which may be empirically determined, and may correspond to the wavelengths of light used. The algorithms may be stored in a ROM 146 and accessed and operated according to microprocessor 122 instructions.

In an embodiment of a two-wavelength system, the particular set of coefficients chosen for any pair of wavelength spectra may be determined by a value indicated by the encoder 116 corresponding to a particular light source in a particular sensor 10. In one embodiment, multiple resistor values may be assigned to select different sets of coefficients. In another embodiment, the same resistors are used to select from among the coefficients appropriate for an infrared source paired with either a near red source or far red source. The selection between whether the near red or far red set will be chosen can be selected with a control input from control inputs 154. Control inputs 154 may be, for instance, a switch on the pulse oximeter, a keyboard, or a port providing instructions from a remote host computer. Furthermore, any number of methods or algorithms may be used to determine a patient's pulse rate, oxygen saturation or any other desired physiological parameter.

In an embodiment, a monitor 100 may provide instructions to vary the emitter drive 132 frequency and/or pattern, and verify that the detected and de-multiplexed light signals are unaffected. Accordingly, when the sensor is receiving a significant portion of its signals from the ambient light (i.e. corresponding to a "sensor off" condition), then a change in the emitter 16 drive frequency and/or pattern will likely result in a change in the detected photocurrent and/or the de-multiplexed waveform (resulting from a change in alias frequencies). This technique may be more advantageous in a setting with sufficient ambient light.

In an embodiment, the sensor 10 includes an emitter 16 and a detector 18 that may be of any suitable type. For example, the emitter 16 may be one or more light emitting diodes adapted to transmit one or more wavelengths of light in the red to infrared range, and the detector 18 may one or more photodetectors selected to receive light in the range or ranges emitted from the emitter 16. Alternatively, an emitter 16 may also be a laser diode or a vertical cavity surface emitting laser (VCSEL), or other light source. The emitter 16 and detector 18 may also include optical fiber sensing elements.

In an embodiment, an emitter 16 may include a broadband or "white light" source, and the detector could include any of a variety of elements for selecting specific wavelengths, such as reflective or refractive elements or interferometers. These types of emitters and/or detectors may be coupled to the rigid or rigidified sensor via fiber optics.

In an embodiment, a sensor 10 may sense light detected from the tissue at a different wavelength from the light emitted into the tissue. Such sensors may be adapted to sense fluorescence, phosphorescence, Raman scattering, Rayleigh scattering, and/or multi-photon events or photoacoustic effects. For pulse oximetry applications using either transmission or reflectance type sensors the oxygen saturation of the patient's arterial blood may be determined using two or more wavelengths of light, most commonly red and near infrared wavelengths. Similarly, in other applications, a tissue water fraction (or other tissue constituent related metric) or a concentration of one or more biochemical components in an aqueous environment may be measured using two or more wavelengths of light. In various embodiments, these wavelengths may be infrared wavelengths between about 1,000 nm to about 2,500 nm.

It should be understood that, as used herein, the term "light" may refer to one or more of ultrasound, radio, microwave, millimeter wave, infrared, visible, ultraviolet, gamma ray or X-ray electromagnetic radiation, and may also include any wavelength within the ultrasound, radio, microwave, millimeter wave, infrared, visible, ultraviolet, or X-ray spectra, and that any suitable wavelength of light may be appropriate for use with the present techniques.

In an embodiment, the emitter 16 and the detector 18 may be disposed on or generally adjacent to a sensor body 14, which may be made of any suitable material, such as plastic, foam, woven material, or paper. In an embodiment, the emitter 16 and the detector 18 may be remotely located and optically coupled to the sensor 10 using optical fibers. In various embodiments, the sensor 10 is coupled to a cable 20 that is responsible for transmitting electrical and/or optical signals to and from the emitter 16 and detector 18 of the sensor 10. The cable 20 may be permanently coupled to the sensor 10, or it may be removably coupled to the sensor 10—the latter alternative being more useful and cost efficient in situations where the sensor 10 is disposable.

In various embodiments, the sensor 10 may be a "transmission type" sensor. Transmission type sensors may include an emitter 16 and detector 18 that are placed on opposing sides of the sensor site. If the sensor site is a fingertip, for example, the sensor 10 is positioned over the patient's fingertip such that the emitter 16 and detector 18 lie on either side of the patient's nail bed. In other words, the sensor 10 is positioned so that the emitter 16 is located on the patient's fingernail and the detector 18 is located 180° opposite the emitter 16 on the patient's finger pad.

During operation, the emitter 16 shines one or more wavelengths of light through the patient's fingertip, and the light received by the detector 18 is processed to determine various physiological characteristics of the patient. In each of the embodiments discussed herein, it should be understood that the locations of the emitter 16 and the detector 18 may be exchanged. For example, the detector 18 may be located at the top of the finger and the emitter 16 may be located underneath the finger. In either arrangement, the sensor 10 may perform in substantially the same manner.

Reflectance type sensors also operate by emitting light into the tissue and detecting the light that is transmitted and scattered by the tissue. Reflectance type sensors may include an emitter 16 and detector 18 which are typically placed on the same side of the sensor site. For example, a reflectance type sensor may be placed on a patient's fingertip or foot such that the emitter 16 and detector 18 lie side-by-side. Reflectance type sensors detect light photons that are scattered back to the detector 18. A sensor 10 may also be a "transflectance" sensor, such as a sensor that may subtend a portion of a baby's heel.

While the resent disclosure may be capable of various modifications and alternative forms, embodiments have been shown by way of example in the drawings and have been described in detail herein. However, it should be understood that the disclosure is not intended to be limited to the particular forms disclosed. Indeed, the present techniques may not only be applied to measurements of blood oxygen saturation, but these techniques may also be utilized for the measurement and/or analysis of other blood constituents. For example, using the same, different, or additional wavelengths, the present techniques may be utilized for the measurement and/or analysis of additional blood or tissue constituents, such as carboxyhemoglobin, met-hemoglobin, total hemoglobin, intravascular dyes, and/or water content. Rather, the disclosure is to cover all modifications, equivalents, and alternatives falling within the spirit and scope of the invention as defined by the following appended claims.

What is claimed is:

1. A system comprising:
a sensor body;
an emitter and a detector disposed adjacent the sensor body; and
a tissue contact sensor disposed adjacent the sensor body, wherein the tissue contact sensor comprises a first temperature sensor configured to measure a temperature of a surface contacting the tissue contact sensor and a second temperature sensor configured to measure an ambient temperature; and
a processor coupled to the tissue contact sensor configured to determine whether the surface is a tissue of a patient by comparing a difference between the measured temperature of the surface and the ambient temperature to a threshold temperature value.

2. The system of claim 1, wherein the temperature sensor comprises a thermistor.

3. The system of claim 1, wherein the second temperature sensor is disposed on a different side of the sensor body than the first temperature sensor.

4. The system of claim 1, wherein the processor is configured to determine that the surface is not the tissue of the patient when the processor determines that the measured temperature of the surface is substantially the same as the measured ambient temperature.

5. A pulse oximetry system comprising:
a pulse oximetry monitor comprising a processor; and a pulse oximetry sensor operatively coupled to the monitor, comprising:
a sensor body;
an emitter and a detector disposed adjacent the sensor body; and
a tissue contact sensor disposed adjacent the sensor body, wherein the tissue contact sensor comprises a first temperature sensor configured to provide a measured surface temperature to the processor of the pulse oximetry monitor and a second temperature sensor configured to provide an ambient temperature to the processor of the pulse oximetry monitor, and wherein the processor of the pulse oximetry monitor is configured to determine whether the sensor is on a patient tissue by comparing a difference between the measured surface temperature and the ambient temperature to a threshold temperature value.

6. The pulse oximetry system of claim 5, wherein the temperature sensor comprises a thermistor.

7. The pulse oximetry system of claim 5, wherein the pulse oximetry monitor is configured to output a "sensor on" notification when the processor determines that the sensor is on the tissue of the patient.

8. The pulse oximetry system of claim 5, wherein the pulse oximetry monitor is configured to output a "sensor off" notification when the processor determines that the sensor is not on the tissue of the patient.

9. A method, comprising:
measuring, with a first temperature sensor disposed on a tissue contacting surface of a pulse oximetry sensor, a first temperature;
measuring, with a second temperature sensor disposed on a non-tissue contacting surface of the pulse oximetry sensor, a second temperature;
determining, with a processor, a difference between the first and second temperatures; and
determining, with the processor, whether the pulse oximetry sensor is on a tissue of a patient based, at least in part, on the difference between the first and second temperatures.

10. The method of claim 9, wherein determining whether the pulse oximetry sensor is on the tissue of a patient comprises determining whether the difference between the first and second temperatures is greater than a threshold value.

11. The method of claim 9, wherein the first temperature sensor and the second temperature sensor comprise thermistors.

12. The method of claim 9, comprising outputting a "sensor on" notification when the processor determines that the pulse oximetry sensor is on the tissue of the patient.

13. The method of claim 9, comprising outputting a "sensor off" notification when the processor determines that the pulse oximetry sensor is not on the tissue of the patient.

\* \* \* \* \*